US009688955B2

(12) United States Patent
Souza

(10) Patent No.: US 9,688,955 B2
(45) Date of Patent: *Jun. 27, 2017

(54) MATERIALS FOR MAGNETIZING CELLS AND MAGNETIC MANIPULATION

(71) Applicant: NANO3D BIOSCIENCES INC., Houston, TX (US)

(72) Inventor: Glauco R. Souza, Houston, TX (US)

(73) Assignee: Nano3D Biosciences, Inc., Houston, TX (US)

( * ) Notice: Subject to any disclaimer, the term of this patent is extended or adjusted under 35 U.S.C. 154(b) by 168 days.

This patent is subject to a terminal disclaimer.

(21) Appl. No.: 14/536,388

(22) Filed: Nov. 7, 2014

(65) Prior Publication Data

US 2015/0104844 A1 Apr. 16, 2015

Related U.S. Application Data

(63) Continuation of application No. 13/393,651, filed as application No. PCT/US2010/050445 on Sep. 27, 2010, now Pat. No. 8,883,471.

(60) Provisional application No. 61/245,846, filed on Sep. 25, 2009.

(51) Int. Cl.
| | |
|---|---|
| *C12N 13/00* | (2006.01) |
| *C12N 5/00* | (2006.01) |
| *C12N 5/07* | (2010.01) |
| *C12Q 1/02* | (2006.01) |
| *C12Q 1/24* | (2006.01) |
| *B03C 1/015* | (2006.01) |
| *B03C 1/30* | (2006.01) |
| *B82Y 25/00* | (2011.01) |
| *G01N 33/543* | (2006.01) |
| *G01N 33/544* | (2006.01) |
| *G01R 33/12* | (2006.01) |
| *H01F 1/00* | (2006.01) |
| *H01F 1/08* | (2006.01) |
| *H01F 1/113* | (2006.01) |
| *H01F 1/44* | (2006.01) |
| *C40B 30/04* | (2006.01) |
| *G01N 33/566* | (2006.01) |
| *G01N 33/68* | (2006.01) |

(52) U.S. Cl.
CPC ............ *C12N 5/0062* (2013.01); *B03C 1/015* (2013.01); *B03C 1/30* (2013.01); *B82Y 25/00* (2013.01); *C12N 5/00* (2013.01); *G01N 33/544* (2013.01); *G01N 33/54326* (2013.01); *G01R 33/1269* (2013.01); *H01F 1/0045* (2013.01); *H01F 1/0063* (2013.01); *H01F 1/083* (2013.01); *H01F 1/113* (2013.01); *H01F 1/445* (2013.01); *B03C 2201/26* (2013.01); *C12N 2513/00* (2013.01); *C12N 2529/00* (2013.01); *C12N 2531/00* (2013.01); *C12N 2533/10* (2013.01); *C12N 2533/32* (2013.01); *Y10S 977/773* (2013.01); *Y10S 977/89* (2013.01); *Y10S 977/904* (2013.01); *Y10S 977/923* (2013.01)

(58) Field of Classification Search
USPC ... 435/29, 173, 173.1, 325, 7.92, 7.93, 7.94; 977/773, 904, 923, 890; 436/501
IPC ................. C12N 5/00,13/00, 5/07; C12Q 1/02, C12Q 1/24; C40B 30/04; G01N 33/566, 33/68
See application file for complete search history.

(56) References Cited

U.S. PATENT DOCUMENTS

| | | | | |
|---|---|---|---|---|
| 8,883,471 | B2 * | 11/2014 | Souza | ..................... B03C 1/015 435/173.1 |
| 2002/0086842 | A1 * | 7/2002 | Plank | ..................... C12N 15/87 514/44 R |
| 2006/0063252 | A1 * | 3/2006 | Ito | ......................... C12M 25/00 435/289.1 |

FOREIGN PATENT DOCUMENTS

WO WO2007029980 3/2007

OTHER PUBLICATIONS

Verma et al. 2003. Particle size of liposomes influences dermal delivery of substances into skin. International Journal of Pharmaceutics, vol. 258, pp. 141-151.*
Li et al. 2006. . Growth of ameloblast-lineage cells in a three-dimensional Matrigel environment. European Journal of Oral Sciences, vol. 114, supplement 1, pp. 159-163.*
Ito et al. 2005. Novel Methodology for Fabrication of Tissue-Engineered Tubular Constructs Using Magnetite Nanoparticles and Magnetic Force. Tissue Engineering, vol. 11, No. 9/10, pp. 1553-1561.*
EP10819626 Search Report.

(Continued)

*Primary Examiner* — Debbie K Ware
*Assistant Examiner* — Kailash C Srivastava
(74) *Attorney, Agent, or Firm* — Boulware & Valoir

(57) ABSTRACT

A material comprising positively and negatively charged nanoparticles, wherein one of said nanoparticles contained a magnetically responsive element, are combined with a support molecule, which is a long natural or synthetic molecule or polymer to make a magnetic nanoparticle assembly. When the magnetic nanoparticle assembly is combined with cells, it will magnetize those cells. The magnetized cells can then be washed to remove the magnetic nanoparticle assembly and the magnetized cells manipulated in a magnetic field.

13 Claims, 10 Drawing Sheets

(56) References Cited

OTHER PUBLICATIONS

Xiaoliang Wang et al: 11 Charged Magnetic Nanoparticles for Enhancing Gene Transfection 11, IEEE Transactions on Nanotechnology. vol. 8. No. 2. Mar. 1, 2009 (Mar. 1, 2009), pp. 142-147.
Rue!-Zeng Lin et al: 11 Magnetic Reconstruction of Three-Dimensional Tissues from Multicellular Spheroids—. Tissue Engineering Part C: Methods. vol. 14. No. 3. Sep. 1, 2008, pp. 197-205.

* cited by examiner

Figure 9a-e a) 2600G ring magnet under dish
b) 3900G ring magnet under dish
b) 3900G ring magnet under dish
c) 1000G ring magnet 8 mm from bottom of dish, cells more diffuse
d) 1000G ring magnet 4 mm from bottom of dish
e) ~30° tilt 1000G ring magnet under dish, cells thicker on one side

MATERIALS FOR MAGNETIZING CELLS AND MAGNETIC MANIPULATION

CROSS-REFERENCE TO RELATED APPLICATIONS

This application claims priority to U.S. Provisional Application No. 61/245,846, which was filed on Sep. 25, 2009, and PCT Application No. PCT/US10/50445, which was filed on Sep. 27, 2010, and U.S. Application No. 13/393,651, which was filed on Mar. 1, 2012, now U.S. Pat. No. 8,883,471, each of which is incorporated by reference in its entirety.

FEDERALLY SPONSORED RESEARCH STATEMENT

Not applicable.

REFERENCE TO MICROFICHE APPENDIX

Not applicable.

FIELD OF THE INVENTION

The invention relates to the fields of nanotechnology, materials, biosynthesis, medicine, cellular biology, and tissue engineering. More particularly, the compositions and methods of the present disclosure relate to methods of magnetizing cells, and 3D cell culturing, cell manipulation, and cell patterning using magnetic fields.

BACKGROUND OF THE INVENTION

Manipulating cells, controlling their environment, and promoting conditions that mimic or illicit in vivo or natural cellular or tissue responses is an area of intense research. In the area of stem cells and regenerative medicine there is a particular need for methods and materials that replicate the native conditions where cells grow in vivo. Conditions that cells experience when removed from their native environment promote homeostasis, where cells change to adapt to their new environment, thus inducing cellular changes. Many of these processes are not elastic or reversible, therefore, cells cannot return to their native state. There is a strong need for materials and methods that promote natural cellular environments and minimize or control adverse cellular changes before cell and tissue engineering can reach its full potential.

Currently, materials are being developed that can support three-dimensional (3D) cell culturing conditions. Most of the work in 3D cell culture techniques involves either rotation of the flasks, the use of an exterior scaffold to which the cells can adhere, the use a magnetic fields to suspend cells, or some combination of these approaches.

For example, Felder in US2005054101, WO2005010162 describes a hydrogel substrate that forms an exterior scaffolding in which cells can grow and be supported in a 3D environment. This introduces an artificial substrate with which cells interact, rather than rapidly promoting cell-cell interactions, and although an improvement over 2D culturing, the scaffolding is likely to perturb the cells and remains in the finished product. Further, cells can grow on or in the microcarriers, but cells cannot be levitated in a manner where all around cell-cell contact/interaction is possible.

Nationally, there is a significant level of complexity involved in the fabrication of the microcarriers of Felder, which includes laborious chemistry and the need for complex equipment. Further, algimatrix, one of the main reagents in making the microcarriers, can be a source of endotoxins. Buoyancy control also seems to be relevant to facilitate levitation, and is controlled by the infusion of glass bubbles into the microcarriers, again contributing to complexity and difficulty. Finally, specialized hardware is required for agitation, which is needed achieve gas exchange and to prevent clumping of the microcarriers, and impellers are often used to agitate cells. However, the shear stress resulting from agitation is known to cause cell damage. Furthermore, agitation impairs any magnetic field shape control of 3D cultures.

Becker in US2009137018, WO2005003332 uses a coating of bioattractive magnetized core particles, thereby initiating adherence of the biological cells to the magnetized core particles and allowing their suspension in a magnetic field. The coating remains with the cells during culture, thus introducing an unnatural element in the culture and probably perturbing the cells. The inventors contemplate the use of a biodegradable coating that could eventually be eliminated, but none are disclosed, so it is not known if this approach would be successful. Furthermore, because cells are grown on the core of the microcarriers, the levitation of individual cells in which they can be brought together by magnetic levitation for the purpose of promoting cell-cell interaction is unlikely to take place. Therefore, it is not obvious that the rapid (hours) assembly of 3D multicellular structures due to cell-cell contact can be demonstrated when using microcarriers. Also, by growing cells on the microcarriers, the co-culture of different cells types, especially by levitating individual cells and then bringing them together magnetically, is not demonstrated. Finally, this system is cumbersome and not suitable for scale-up and high-throughput applications.

A better approach might be to temporarily magnetize cells, allowing for their 3D culture. For example, Akira in US2006063252, WO2004083412, WO2004083416 uses magnetic cationic liposomes (MCL) to magnetize cells by uptake of the liposomes. The magnetized cells are then grown in a sheet on the bottom of a plate using magnetic attraction, and then released for use. However, although able to produce sheets of cells, the cells are still grown on the bottom of a plate, and thus this is not true 3D culturing by magnetic levitation. Further, Shimizu and Akira et al. in a recent publication entitled "Effective Cell-Seeding Technique Using Magnetite Nanoparticles and Magnetic Force onto Decellularized Blood Vessels for Vascular Tissue Engineering" use magnetic guidance to seed cells onto a decellularized blood vessel.[1] Their study shows encouraging results, but they do not use the magnetized cells as the source of tissue to be decellularized. The magnetized cells are only used to recellularize the decellularized blood vessels.

In patent application WO2010036957 by Souza, cells are levitated in a magnetic field by contacting the cells with a "hydrogel" comprising a bacteriophage with nanoparticles that are responsive to a magnetic field. In particular, filamentous phage, such as fd, fl, or M13 bacteriophage, are used. How the method works is not completely clear, but it is theorized that the phage provide a gel-like structure or assembly that coats the cells, and somehow assists the cells to uptake or adsorb the magnetically responsive nanoparticles. Thus, even when the hydrogel is washed away, the cells remains magnetically responsive, and can be levitated in an appropriate magnetic field. However, although the hydrogel is mostly washed away, the potential for phage infectivity or transfer of genetic material remains, and thus it is desired to provide a material that allows cell uptake or adsorption without the use of phage.

The present disclosure overcomes the shortcomings existing in the art by providing improved materials and methods that promote native cellular environments. These include utilizing compositions and methods for generating nanoparticle-based materials and preparing cells to enable 3D cell culturing, cell patterning, and cell imaging.

SUMMARY OF THE INVENTION

As used herein a "positively charged nanoparticle" or "positive nanoparticle" is defined as any particle less than 200 nm, preferably 100 nm or less, that has an over all positive charge. Preferably, the particle is non-toxic, but this is not essential as the particles do not remain with the cells.

As used herein a "negatively charged nanoparticle" or negative nanoparticle" is defined as any particle less than 200 nm, preferably 100 nm or less, and most preferably about 2-25 nm, that has an over all negative charge. Preferably, the particle is non-toxic, but this is not essential as the particles do not remain with the cells for a long period of time.

As used herein a "magnetically responsive element" can be any element or molecule that will respond to a magnetic field. As detailed below, one of the nanoparticles must contain or be a magnetically responsive element.

As used herein "support molecule" refers to any long molecule that will interact with the nanoparticles to create a mat like fibrous structure or gel and thus hold the magnetic nanoparticle in close proximity with the cell for uptake.

The following abbreviations are used herein:

| Abbreviation | |
|---|---|
| +NP | positively charged nanoparticle |
| COL | collagen |
| Fluor G | AlexaFluor 555 Anti-Mouse IgG |
| Fluor R | AlexaFluor 488 donkey Anti-Rabbit IgG |
| FN | fibronectin |
| HYA | hyaluronic acid |
| IgG | immunoglobulin G |
| IgG-FR | mouse IgG and AlexaFluor 555 donkey anti-mouse immunoglobulin G |
| LM | laminin |
| MG | matrigel |
| −NP | negatively charged nanoparticle |
| NT | oligonucleotides |
| PL | poly-lysine |
| SER | fetal bovine serum |
| SM | support molecule |

Generally speaking, the invention is a new material that allows cells to uptake or adsorb magnetically responsive elements, and thus be levitatable in cell culture when a magnetic field is applied. The materials include positively and negatively charged nanoparticles, one of which must contain one or more magnetically responsive elements, such as iron oxide. These nanoparticles are further combined with a polymer, preferably a natural or cell derived polymer, or other long molecule that acts as a support (herein called a "support molecule") for the charged nanoparticles and the cells, holding the nanoparticles in place for their uptake or adsorption by the cells. The inclusion of both positive and negative nanoparticles allows intimate admixing of the nanoparticles and drives the assembly of the three components, thus ensuring even distribution and good uptake. The support molecule intimately combines all three components with the cells in fibrous mat-like structure that allows the cells to take up the magnetically responsive element.

After a period of incubation, the material can be washed away, allowing the cells to be manipulated in a magnetic field. An alternative step is to optimize or tune the uptake of magnetic material by increasing the ratio between the number of cells and the amount of magnetic nanoparticle. If a large number of cells are present they will uptake most of the magnetic nanoparticles, and the step of washing way any leftover material may no be necessary, particularly if the remaining support molecules and/or nanoparticles are non-toxic and/or beneficial to the cell. This is particularly true where the support molecules comprise one or more extracellular matrix protein, glycoprotein or polysaccharide. The magnetic particles are eventually lost from the cells, leaving them in a completely natural state.

In addition to simple 3D culturing, the magnetic field can be used to manipulate cell shape, patterns and motion. For example, the use of a toroidal (washer shaped) magnet can promote the cells to assemble into a similar shape or a tilted field can make the 3D cell culture thicker on one side. We have also created firm dense sheets of cells, by placing a strong magnet at the bottom of a culture dish for a period of growth. Simply reversing the field, allows the sheet to then be levitated and we can then continue growing the sheet in a 3D culture. It is also possible to combine various shapes and continue 3D culturing and thus create more complex shapes in a 3D culture.

The magnetically responsive element can be any element or molecule that will respond to a magnetic field, e.g., rare earth magnets (e.g., samarium cobalt (SmCo) and neodymium iron boron (NdFeB)), ceramic magnet materials (e.g., strontium ferrite), the magnetic elements (e.g., iron, cobalt, and nickel and their alloys and oxides). Particularly preferred are paramagnetic materials that react to a magnetic field, but are not magnets themselves, as this allows for easier assembly of the materials.

Preferably, the magnetic field used to levitate such cells is about 300 G-1000 G. However, the field strength varies with both distance from the cell, and with the amount and type of magnetic response element taken up or adsorbed by the cells. Thus, the optimal field strength will vary, but is easily determined empirically.

The negatively charged nanoparticles include charge stabilized metals (e.g. silver, copper, platinum, palladium), but preferably is a gold nanoparticle.

The positively charged nanoparticles include surfactant or polymer stabilized or coated alloys and/or oxides (e.g. elementary iron, iron-cobalt, nickel oxide), and preferably is an iron oxide nanoparticle.

One of the two nanoparticles must be magnetically responsive, but obviously either one could contain this feature.

The nanoparticles should have a nano-scale size, and thus are about 100 nm. Size can range, however, between about 5-250 nm, 50-200 nm, 75-150 nm, but they can be smaller or larger, provided only that the size is appropriate to allow entry or adsorption to the cell type in use. We have shown herein that there is an upper limit on the effective size of the magnetic nanoparticle, and micrometer size is too big for effectiveness, although some functionality was still observed.

The "support molecule" is generally a polymer or other long molecule that serves to hold the nanoparticles and cells together in an intimate admixture. The support molecule can be positively charged, negatively charged, of mixed charge, or neutral, and can be combinations of more than one support molecule.

Examples of such support molecules include the natural polymers, such as peptides, polysaccharides, nucleic acids, and the like, but synthetic polymers can also be employed. Particularly preferred support molecules include poly-lysine, fibronectin, collagen, laminin, BSA, hyaluronan, glycosaminoglycan, anionic, non-sulfated glycosaminoglycan, gelatin, nucleic acid, extracellular matrix protein mixtures, matrigel, antibodies, and mixtures and derivatives thereof.

Generally speaking, the concentration of the support molecule is substantially greater than the concentration of the negatively and positively charged nanoparticles, ranging from 1-1000 fold greater, 10-500, or 20-200 fold greater. However, greater or lesser amounts are possible, depending on what cell type is being used and which support molecule and nanoparticles are being used. The longer the polymer, the less may be needed to form sufficient structure to hold the nanoparticles in place for uptake.

Generally, the nanoparticles are used in very low concentrations. Concentrations can range between $10^{-12}$-$10^{-6}$ Molar, but are preferably in the nanomolar range, and the support molecule(s) $10^{-9}$-$10^{-3}$ Molar, and are preferably in the micromolar range.

The three components assemble by electrostatic interaction, and thus charged or mixed charge support molecules, such as poly-lysine, are preferred. However, any of the three components can be functionalized, derivatized, or coated so as to further promote interaction of the components and/or the cells. Thus, one or more members can be functionalized, derivatized, or coated with an antibody that e.g., binds to a cell surface antigen. Thus, interactions between the components and/or the cells would be further promoted. Other binding pairs included receptors-ligands, biotin-strepavidin, complementary nucleic acids, wheat germ agglutinin (WGA), sialic acid containing molecules, and the like.

Coatings can also include protective or passivating coatings, particularly for the nanoparticles, such as PVP, dextran, BSA, PEG, and the like. The nanoparticles, especially the nanoparticle that comprises the magnetically responsive element, can be labeled for visualization, e.g., with a fluorophore, radiolabel, or the like, particularly during the development and in vitro testing of magnetized cells and tissues. However, for therapeutic uses, it may be preferred to omit such labels.

In other embodiments, the compositions include the cells that will be levitated or manipulated in a magnetic field, including, but not limited to, stem cells, cancer cells, primary cells, mammalian cells, human cells, cells extracted directly from fresh tissue, bacteria, yeast, plant cells, or mixtures thereof.

The present disclosure also provides methods of culturing cells, patterning cells, and imaging cells in three-dimensions, comprising mixing the cells with one or more of the presently disclosed compositions and culturing, patterning, or manipulating the mixture in the presence of a magnetic field. The magnetic field can be above or below the culture container, closer or farther (e.g, stronger or weaker), be tilted or to the side, or the shape of the field can be varied, or combinations of one or more of the same can be applied. In this way the cells can be patterned or moved to achieve particular goals.

Our extensive testing of the above described system has shown there are a great number of improvements now made available over the prior art methods. First, the self assembly manufacturing chemistry makes the method simple and reproducible, and no specialized equipment is required for the manufacture of the magnetic nanoparticle assembly, or for subsequent cell magnetizing, manipulation or 3D culturing. The only requirements were a magnetic field, pipettes, containers and a hot plate. Thus, the method is compatible with large scale and high-throughput.

If desired the magnetic nanoparticle assembly can be made free from biological molecules, such as phage or cell products because the support molecules, such as poly-lysine, can easily be made synthetically. Yet all of the components are generally non-toxic, inexpensive or easy to make. Further, the fibrous mat like structures allows for the incorporation of additional cell support molecules (such as extracellular matrix components) to be included into the nanoparticle magnetic assemblies.

Magnetizing cells with magnetic nanoparticle assemblies consists of only adding assembly to cells in regular cell culture media. Cells can be magnetized within minutes from magnetic nanoparticle treatment (5 minutes) and either attached or suspended cells can be treated with magnetic nanoparticle assemblies. Cells can be cryopreserved before or after treatment with magnetic nanoparticles and the method still works. If desired the magnetic nanoparticle assembly can be washed off the magnetized cells before use, and the remaining cells will still levitate.

Levitating and culturing cells in 3D by magnetic levitation does not require any specialized or costly equipment or methods (such as for agitating or maintaining buoyancy) beyond standard 2D cell culturing requirements, and shape control of magnetically levitated 3D cell culture can be achieved by varying the magnetic field shape. Finally, and perhaps most importantly, the invention promotes rapid cell-cell interaction (scale of seconds and minutes) with levitation of cells and assembly into 3D multicellular clusters within minutes, and that complex culture structures can be made by manipulating the magnetic field and/or by magnetically bringing different cell types into contact.

DESCRIPTION OF EMBODIMENTS OF THE INVENTION

The present disclosure provides compositions comprising negatively charged nanoparticles, positively charged nanoparticles, and a support molecule comprising a polymer or long molecule, or metal-binding polymer or molecule. The following examples are illustrative only, and not intended to unduly limit the invention.

EXAMPLE 1

Magnetic Nanoparticle Assemblies

Figure 1:
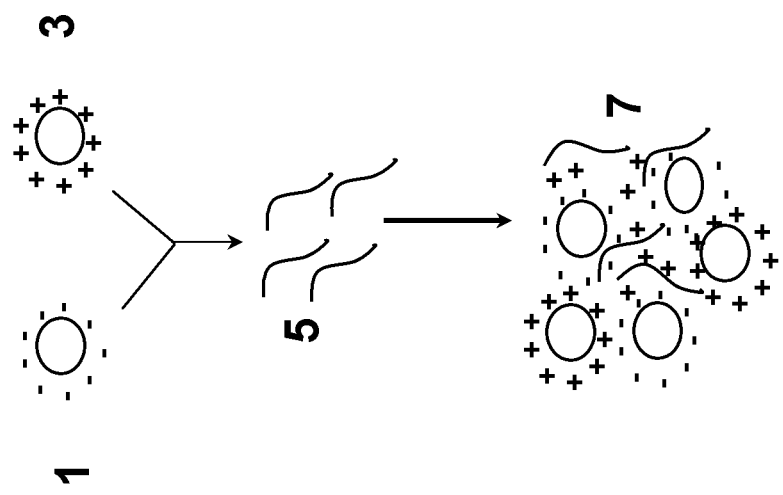
FIG. 1. A schematic for a direct assembly method for generating nanoparticle assemblies. In this diagram, 1 is the negatively charged nanoparticle, 3 is the positively charged nanoparticle, and 5 is support molecule and the completed magnetic nanoparticle assembly is 7. The three components can be combined in any order, but here is shown the nanoparticles first combined and then added to the support molecule.

FIG. 1 shows a general scheme for preparing magnetic nanoparticle assemblies (7) by combining negative nanoparticles (1) and positive nanoparticles (3) (at least one nanoparticle being of magnetic nature) and support molecules (5).

Solutions of nanoparticles are prepared by separately mixing the nanoparticles in water or low ionic strength buffer (salt concentration <10 mM) at a desired pH. The particle surface charge can be adjusted by choosing the appropriate pH, where low pH buffer (such as citrate or carbonate buffer) can generally increase the overall charge on the nanoparticles. In contrast, high pH buffer (such as borate buffer) can generally decrease the overall charge on the particles. Ideally, the pH of choice for each solution should result in opposite charges between the two particles. This can be achieved because nanoparticles of different composition usually have distinct isoelectric points.

For example, Au nanoparticles are negatively charged at most pH values, often due to the presence of citrate or chloride adsorbed ions, in contrast to iron oxide nanoparticles, which can vary from pH=3.3-8, [2] depending on the type of the iron oxide. Therefore at pH 4, Au nanoparticles are expected to be negatively charged and iron oxide nanoparticles should be positively charged. Nanoparticles can also be coated with molecules, such as dextran, polyethylene glycol, or thiols, which can dictate the overall charge of the nanoparticles as well. A mismatch of charges is desirable to ensure that assembly takes place with support molecules that are either positively, negatively charged, mixed, or neutral.

Solutions of support molecules (5) are generally prepared by solubilizing or mixing them with water or buffered solutions (such as citrate, phosphate, borate) of a desired pH and preferably low ionic strength (preferably, salt concentration <10 mM, but salt concentration could be higher if needed to assure molecule solubilization). Low ionic strength is generally desirable to reduce charge screening, and therefore promote charge interaction between nanoparticles and polymers of opposite charges. The concentrations of support molecules (5) should generally be in excess of the nanoparticle concentration (10 nM to 1 mM range, but other concentrations can be used), usually in excess of 10× relative to the molar concentrations of nanoparticles (1) and (3).

In further detail, the support molecule can also provide functionality to the assembly, such as: improving the magnetic nanoparticles adhesion to cells (such as poly-lysine); improve the cell culturing environment (such as by using extracellular matrix proteins, such as collagen and laminin); enable the delivery of a specific molecule (such as DNA, drugs, ligands, labels, etc.) to cells; provide function as signal reporters (such as fluorescence label); and/or improve cell/tissue bio-compatibility of the magnetic nanoparticle assemblies (e.g., by providing nutritional support, or a compatible immunosurface, and the like).

Figure 2:
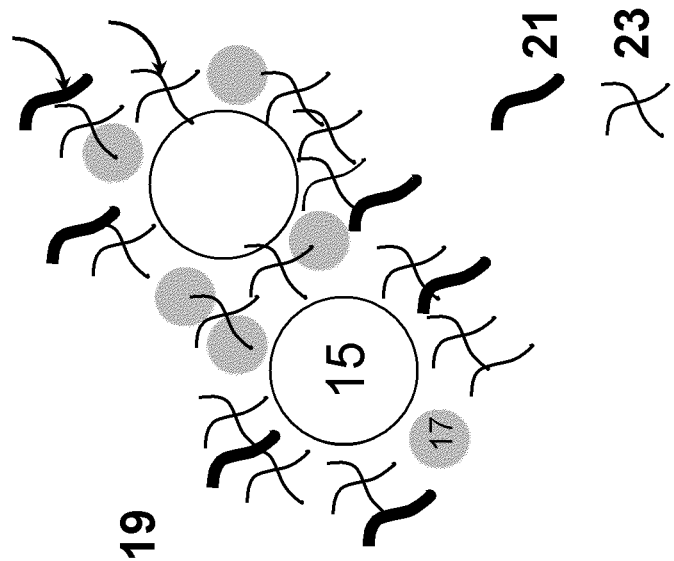
FIG. 2. A schematic showing a variant magnetic nanoparticle assembly 19. The positive nanoparticle is 15, the negative nanoparticle is 17, and 21 and 23 reference two different support molecules, e.g., poly-lysine (+ charge) and a peptide rich in glutamate and/or aspartate (− charge), or as another example, laminin and fibronectin.

FIG. 2 shows a magnetic nanoparticle assemble (19) where the negatively charged nanoparticle (17) and positively charge nanoparticle (15) are held by two support molecules (21, 23). One example of pairing support molecules, could be laminin and fibronectin, another might be antibody and antigen.

We have prepared a wide variety off magnetic nanoparticle assemblies, and tested their functionality with various cells in various media. Table 3 shows the range of components tested:

TABLE 3

Tested Materials

| +NP | −NP | SM | CELL |
|---|---|---|---|
| 74 nm Au (1 pmol to 1 nmol) | ,<50 nm $Fe_2O_3$ (0.01 to 10 mg/ml) | PL 0.01-0.00001% | HEK293 |
| 50 nm Au (1 pmol to 10 nmol) | Ferridex (0.01 to 10 mg/ml) | FN 0.05% to 0.0001% | H4IIE cancer cells (rat hepatocarcinoma) |
| 2 nm Au (1 pmol to 100 nmol) | <5 μm $Fe_3O_4$ (0.001 to 1 mg/ml) | LM 10 μg/ml–1 mg/mL | 3T3-fibroblasts (Pre-adipocytes) |
| | | COL 0.1% to 0.005% and/or 0.30 μg/ml to 0.05 μg/ml | Human Astrocytes |
| | | SER 50% to 0.5% | Heart Valve endothelial cells |

TABLE 3-continued

| | | Tested Materials | |
|---|---|---|---|
| +NP | −NP | SM | CELL |
| | | HYA<br>10 mg/ml to 0.1 mg/ml<br>IgG<br>0.5 mg/ml to 0.05 mg/ml<br>Fluor R<br>0.5 mg/ml to 0.05 mg/ml<br>Fluor G<br>0.5 mg/ml to 0.05 mg/ml<br>MG<br>50% to 0.5%<br>FuGENE plus DNA<br>DNA<br>10 µg/ml to 1 µg/ml<br>Mouse IgG - anti-<br>mouse IgG-FR<br>0.5 mg/ml to 0.05 mg/ml | Human primary tracheal smooth muscle cells<br>Human primary pulmonary fibroblasts<br>Human primary small airway epithelial cells<br>Human primary Pulmonary Microvascular Endothelial Cells (HPMEC)<br>Human mammary epithelial (MCF10)<br>Glioblastoma (LN229)<br>Human umbilical vein endothelial cells (HUVEC)<br>Rat embryonic stem cells<br><br>Murine Chondrocytes<br>Human Bone Marrow Endothelial Cells (HBMEC)<br>Human Mesenchymal Stem Cells (HMSC)<br>Cells extracted from human dental pulp (including stem cells)<br>Mouse zygote or embryo |

Figure 3:
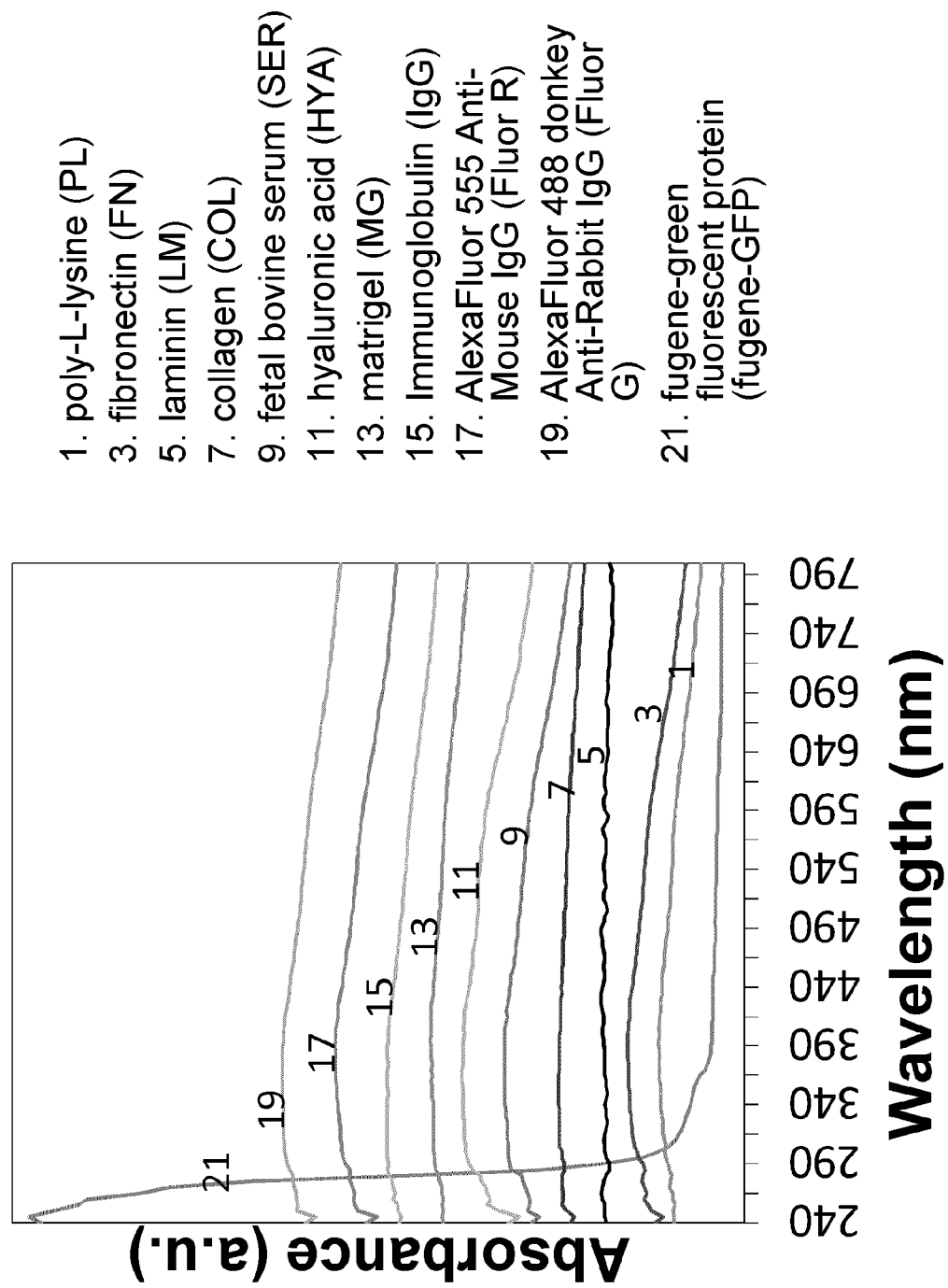
FIG. 3. is the absorbance spectra of actual nanoparticle assemblies composed of magnetic iron oxide and gold nanoparticles and various support molecule(s) as listed to the right.

FIG. 3 shows the absorption spectra of various assemblies. The variations in extinction spectra between different solutions are a result of varying levels of electrostatic cross-linking between the nanoparticles and the various support molecules. With the exception of the spectra for laminin (5), collagen (7), and FuGENE-GFP (21), they all presented a broad shoulder centered approximately at 560 nm, which results from Au nanoparticle characteristic absorption. The nature of the flat spectra relative to Au nanoparticle spectrum is a result from the presence and broad extinction spectra of the polydispersed iron oxide nanoparticles (generally smaller than 100 nm). The spectra for laminin (5) and collagen (7) are the nanoparticle assemblies prepared with extracellular matrix components. The spectra designated as FuGENE-GFP (21) is of nanoparticle assemblies prepared with FuGENE (a liposome) loaded with DNA plasmid encoding a GFP reporter molecule. The presence of the DNA plasmid is indicated by the presence of the UV shoulder at 260 nm (DNA absorbs at 260 nm) in the trace for (21).

Figure 4:
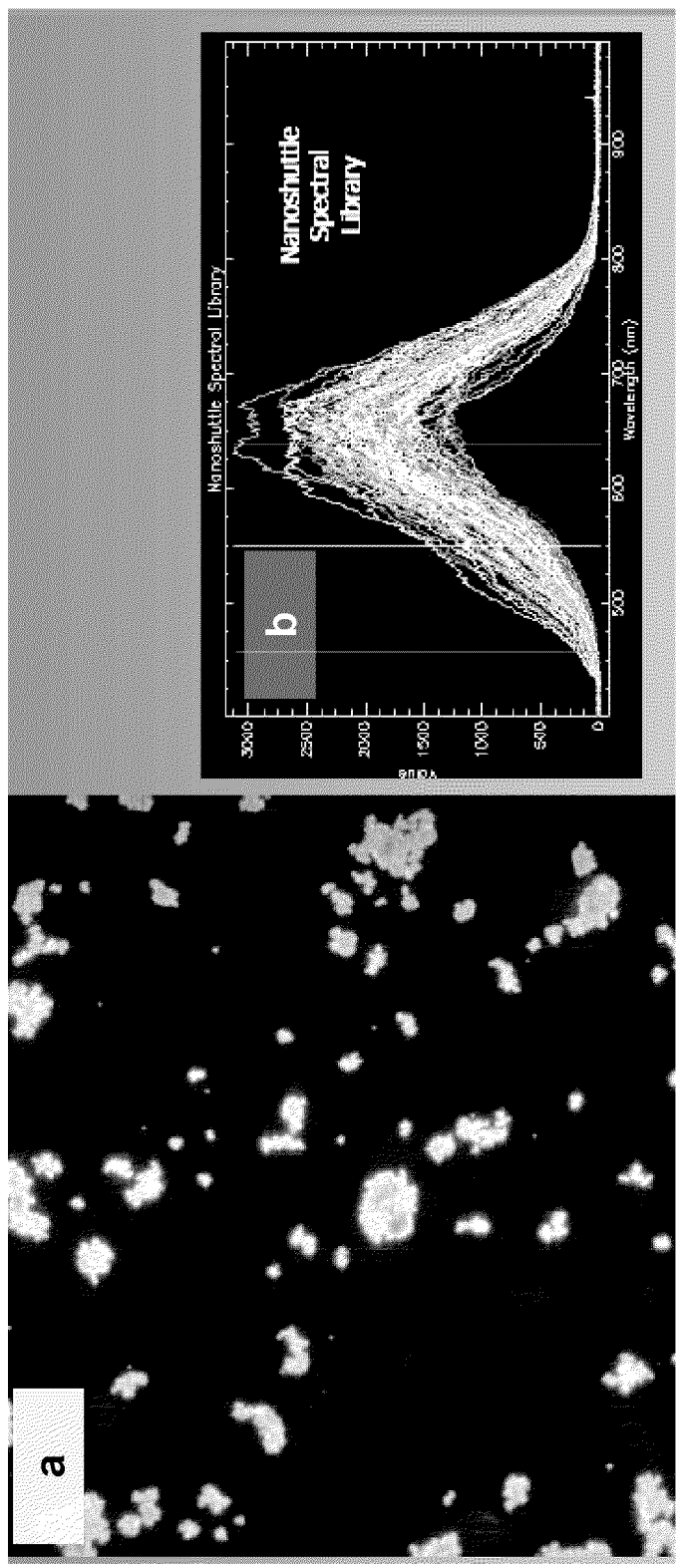
FIG. 4a-b shows the dark-field imaging (a) and hyperspectra (b) of an exemplary FeO2-Au-PL nanoassembly.

FIG. 4 shows the dark-field imaging (a) and hyperspectra (b) of an exemplary $FeO_2$—Au—PL nanoassembly. Hyperspectral imaging is an optical technology combining dark-field-based microscopy with wavelength resolved spectra of scattered light (400-1000 nm) from an imaged sample. This technology enables the identification of nanomaterials based on their optical scattering characteristics. One peak would be expected of monodispersed nanoparticles, but here, the predicted broadening of the spectra is due to the presence of iron oxide nanoparticles and their assembly. Although there is broadening of the spectra, it still provides enough spectral resolution for identifying these samples within a tissue. Thus, this is a method for monitoring the assembly in vitro or in vivo.

Figure 5:
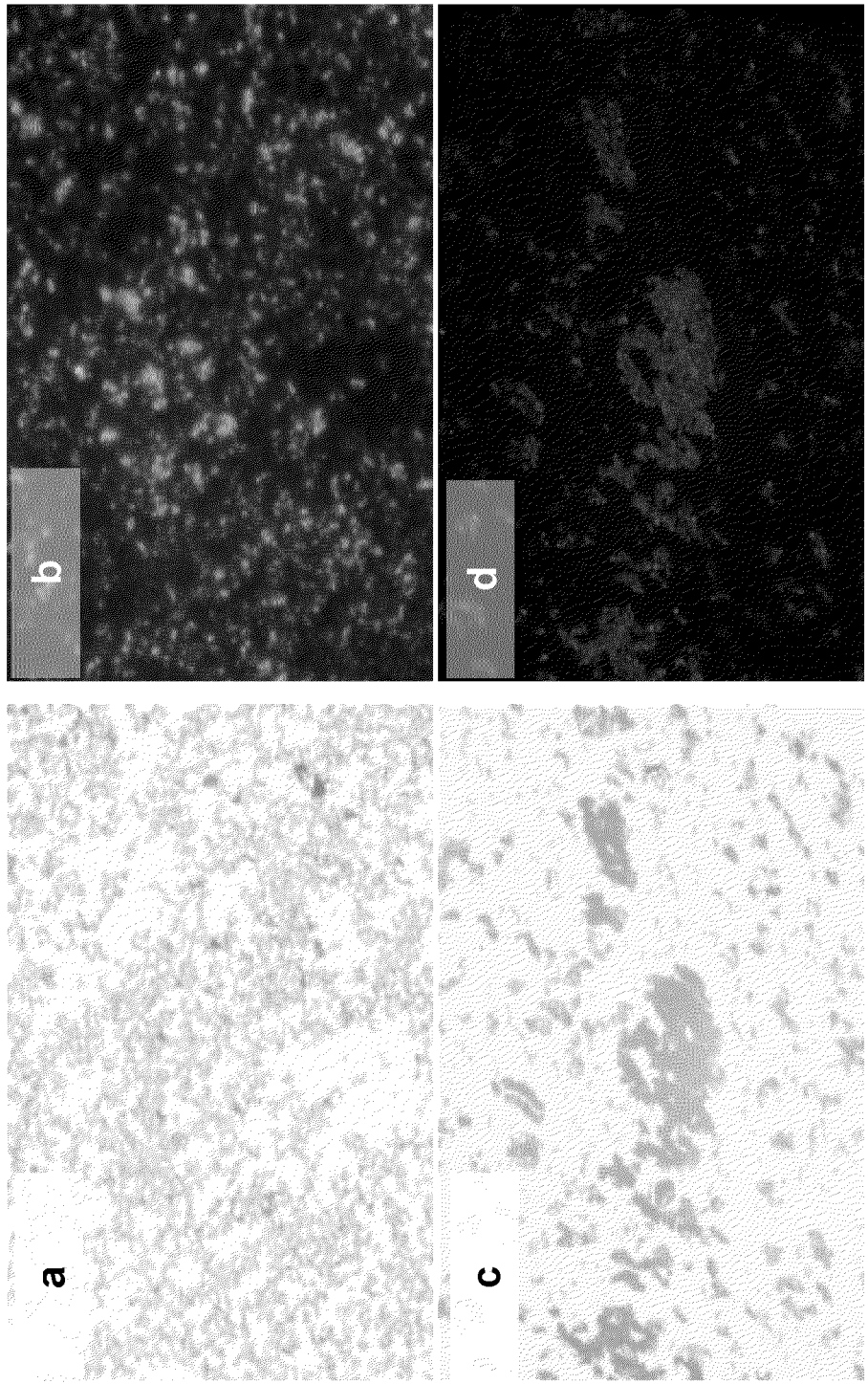
FIG. 5a-d shows brightfield and fluorescent images under 10× magnification. a is a brightfield image with IgG-AlexaFluor 488 support molecule. b is a green fluorescence image of same field. c is the brightfield photo with mouse IgG and anti-mouse IgG AlexaFluor 555 support molecules and d is the red fluorescence image of the same field.
Figure 6:
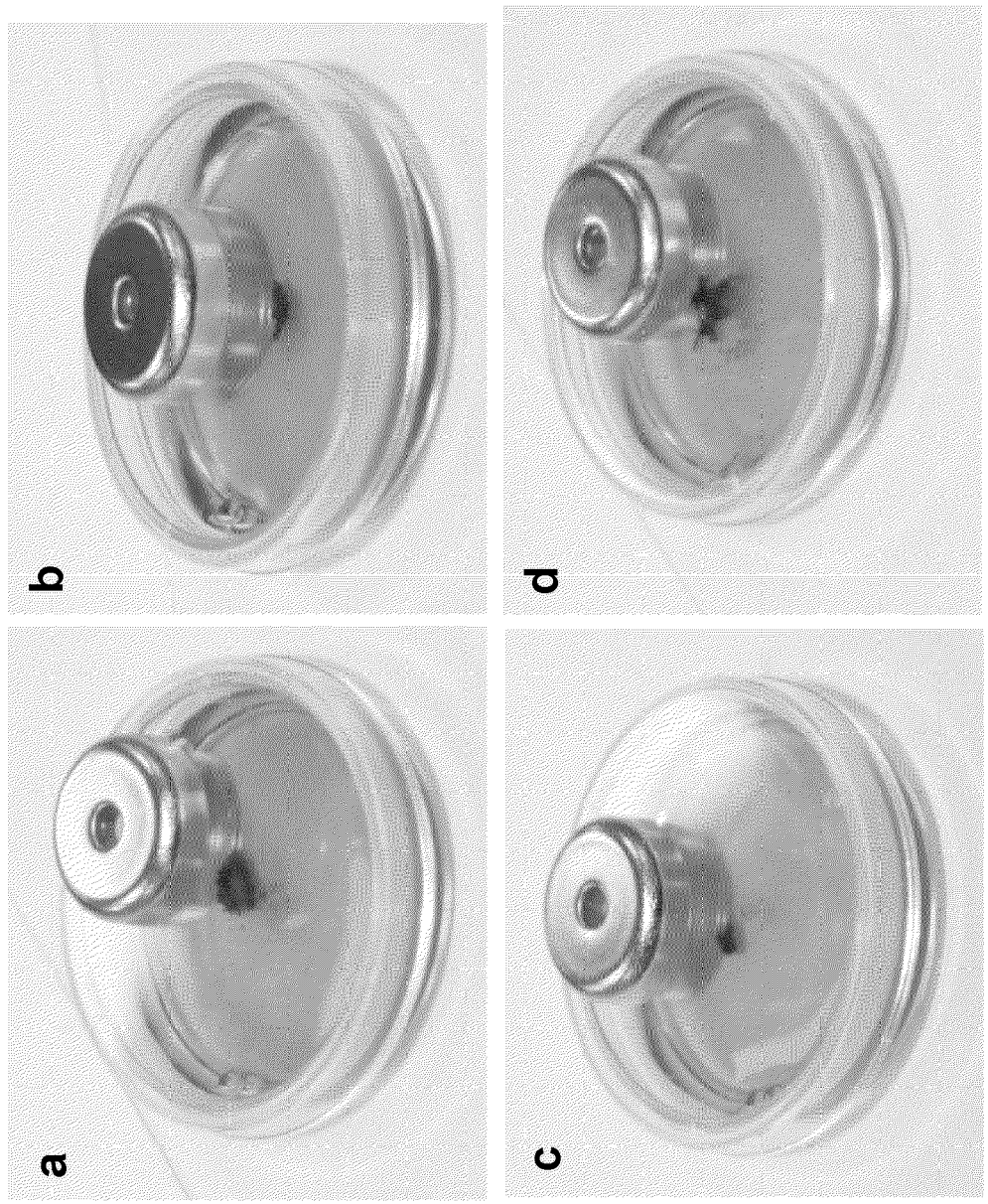
FIG. 6a-d. Photographs of HEK293 cells levitating after treatment with magnetic nanoparticle assemblies of different compositions, including a=PL, b=COL, c=LAM, d=NT.

Now referring to FIG. 5, a fluorescence signal from magnetic nanoassemblies (a, c) prepared with fluorescent protein conjugates as the support molecule (b, d). The nanoparticle assembly shown in images a and c, was generated by using FIG. 1A scheme, using gold and iron oxide nanoparticles, and AlexaFluor 555 donkey Anti-Mouse IgG and protein mouse IgG as a duel support molecules. First gold and iron oxide were mixed, then the protein mouse IgG was added to form a magnetic nanoparticle assembly. Then, in a second/separate step, the assembly was incubated with fluorescence reporting antibody AlexaFluor 555 donkey Anti-Mouse IgG. Thus, the magnetic nanoparticle assembly can be labeled and monitored in use.

FIG. 6a-d shows photographs of cells levitating after treatment with a magnetic nanoparticle assembly of different compositions generated with the method described in FIG. 1. The procedure used was as follows: an iron oxide-Au assembly was generated by first mixing 6 ml of a X mg/ml solution of an approximately 74 nm diameter Au nanoparticle solution (generated by citrate reduction, with 4.1 extinction at the wavelength 548 nm) with 3 ml of a 1.0 mg/ml polydispersed iron oxide nanoparticle solution in picopure water. Then, 1.0 ml of the iron oxide-Au mixture was immediately added to separate 1.0 ml solutions of poly-lysine (at 0.0001%), collagen (at 30 µg/ml), laminin (at 10 µg/ml), or oligonucleotide (at 1 µg/ml) all dissolved in picopure water.

After mixing with support molecules, the solutions were allowed to incubate overnight. The supernatant fraction was removed using magnetic separation, pulling the magnetic nanoparticle assembly to the bottom using a magnet, and the supernatant discarded. To remove the excess unreacted reagents, the magnetic nanoparticle assembly was washed twice with 5 ml of picopure water each time. Then, it was stored in 5 ml of picopure water at 4° C.

Finally, 5 ml of HEK293 cells (50,000 cells/ml) were carefully pipetted in a 15 ml conical tube with 0.5 ml of the nanoparticle assembly. This mixture was gently mixed by pipette action and allowed to incubate and settle for 5 minutes. Then cells were allowed to settle for 5 minutes in the conical tube, and then supernatant was removed (placed in a conical tube) and replaced with culture media. This washing procedure was repeated two more times.

Because cells coupled to the nanoparticle assemblies settle much faster than unbound nanoparticles, the unbound nanoparticles were removed with the supernatant. The unbound nanoparticles can be visually detected in the supernatant by placing a magnet at the bottom of conical tube with the supernatant, and nanoparticles visualized due to magnetic sedimentation. After the third wash, supernatant seemed depleted from free magnetic nanoparticle assemblies. Cells were then transferred to 3.5 cm Petri dish and levitated with a ring shape neodymium magnet (20×(8.5× 4.5)×7 mm; pull strength: 13 lbs). All cells levitated and coalesced into a 3D culture within minutes of applying a magnetic field, regardless of which support molecule(s) were used. Many other support material have been tested herein and all functioned, but only a few exemplary results are shown.

Example

Component Molecules

We have also demonstrated the importance of the various components of the magnetic nanoparticle assembly herein, by testing $Fe_2O_3$ nanoparticles alone, (<50 nm particle size), Au—($Fe_2O_3$) nanoparticles, and complete magnetic nanoparticle assemblies of PL-AU—($Fe_2O_3$).

Cells were treated with samples carrying the same amount of iron oxide magnetic nanoparticles, or approximately 1.0 µl per 5,000 cells, and microphotographs were taken directly after onset of levitation with a 500 G magnet, as well as after cells were cultured by magnetic levitation for 7 days with a 300 G magnet or a 500 G magnet (data not shown).

All cells were able to levitate at one day, however, those samples treated with the PL-AU—($Fe_2O_3$) showed larger and more cohesive 3D structures, especially when cultured with the 500 G magnet. Therefore, all three components are needed for effective cell levitation and coalescence into a 3D structure. Although the nanoparticles alone showed inferior performance, there is still value in the capability to levitate and culture cells that are treated with nanoparticles that require less manipulation than the embodiments in FIG. 1.

Example

Material Delivery to Cells

We have also demonstrated the capability of the magnetic nanoparticle assemblies to carry and deliver materials to cells. As proof-of-principle, HEK293 cells were treated and levitated with the magnetic nanoassemblies carrying GFP DNA, and then GFP fluorescence signal was detected inside the cells of the levitated 3D cell culture.

In further detail, the procedure of preparing the DNA carrying magnetic nanoassemblies was the following: First, FuGENE solutions were prepared according to manufacturer's instructions (Roche Applied Science, FuGENE HD Transfection Reagent), where 2 µg of GFP plasmid DNA (DNA) was dissolved in 200 µl of serum free DMEM medium.

Then, 6 µl of FuGENE solution was added directly into the 200 µl solution of the diluted DNA (FuGENE-DNA). This mixture was allowed to sit for 15 minutes at room temperature. Two other samples were prepared: one with 6 µl of FuGENE added directly into 200 µl of serum free DMEM medium (no DNA, negative control, herein called FuGENE), and another with 4 µg of DNA in 200 µl of serum free DMEM medium (herein called DNA). Then, 3 ml of 2:1 ratio (v/v) of the Au and iron oxide nanoparticle solution (1 mg/mL iron oxide prior to mixing with Au) was combined and mixed thoroughly, and then added directly to 100 µl FuGENE-DNA, 100 µl FuGENE, and 100 µl DNA.

The solution was mixed well and allowed to incubate overnight at 4° C. After an overnight incubation period, the nanoparticles had settled. Extinction spectra were taken of the nanoparticle assemblies composed of magnetic iron oxide and gold nanoparticles and their nanoparticle-free supernatant (collected after the nanoparticles had settled), which indicated the incorporation of the DNA and/or FuGENE from its high UV absorption. The spectra from the supernatant show lower absorbance than the mixed samples, indicating the incorporation of DNA and FuGENE into the nanoparticle assembly.

The magnetic nanoparticle assemblies were added to the cells, and the cells levitated as above, and the levitating cells were then photographed. The presence of GFP fluorescence signal in the cells of both DNA carrying systems (not shown), shows the capability of these magnetic nanoparticle assemblies to carry and deliver DNA to cells while magnetizing and culturing these cells in 3D by magnetic levitation. This result proves that the magnetic nanoparticle assembly can be used to both magnetize cells and to deliver functional materials to the cells, such as DNA or drugs.

Example

Primary Cell Levitation

Primary cells are often difficult to culture in vitro, but we have demonstrated primary cells successfully cultured in 3D by magnetic levitation after they were magnetized with iron oxide-Au—PL.

Various magnetic nanoparticle assemblies were made, including Au nanoparticles, PL, and different iron oxide nanoparticles. The various iron oxides were Ferridex-PL, iron oxide-Au—PL (<50 nm), iron oxide-Au—PL (~5 nm Au), and iron oxide-Au—PL (<5 µm, an example of microparticle). Ferridex is composed of dextran-coated superparamagnetic iron oxide nanoparticles (SPIONs). The isoelectric point (pI) or the pH at which a particular molecule or surface carries no net electrical charge for the following is: SPION, 7;[3-5] magnetite ($\gamma$-$Fe_2O_3$), 3.3-6.7;[2] and magnetite ($Fe_3O_4$), 6.5-6.8.[2]

For the different nanoparticle assemblies the following were used: 11.2 mg/mL Feridex I. V. (Advanced Magnetics, Inc., Cambridge, Mass.), Iron(III) oxide (Sigma Aldrich, 544884, <50 nm particle size, $Fe_2O_3$. This product consists primarily of the gamma-form, magnetite, but both the alpha-form and gamma-form are present in the mineral form naturally). We also used iron (II, III) oxide (Sigma Aldrich, 310069, <5 µm, $Fe_3O_4$, magnetite). All three iron samples were diluted to working solutions of 1 mg/mL in water. The ~5 nm Au colloid was prepared according to Duff et al.[6]

The preparation of iron oxide-Au—PL consisted of six serial dilutions of aqueous poly-L-lysine (PL) with concentrations ranging from $1.00\times10^{-3}$-$3.12\times10^{-5}$%, which were prepared separately. An equal part 1:1 ratio (v/v) of the Au and iron oxide nanoparticle solution was added to each dilution. After an overnight incubation period, the nanoparticles had settled to the bottom of each vial and half the supernatant was removed. Starting with the lowest dilution, the serial dilutions mixtures were combined and mixed with the next lowest dilution in a serial manner until all the solution remained in one vial. The overall PL concentration was $1.24\times10^{-3}$%.

Mixing the reagents as serially diluted samples allows uncoupled reagents from higher dilutions the chance of being incorporated into the assembly. Also, different dilutions often present distinct optical, structural, adhesive, and other physical characteristics; by mixing the different dilutions these properties can be integrated. Often integrating such properties can be desirable. On the other hand, this process can be a good visual diagnostic to determine and choose optimum conditions depending on the application. For example, one or a number of dilutions could be sticky to the plastic or pipettes.

Four types of human primary pulmonary cells (SCIENCELL RESEARCH LABORATORIES,™ Carlsbad, Calif.) were treated with iron oxide-Au—PL assemblies and then cultured in 3D. This procedure consisted of culturing these cells as monolayers to ~80% confluence in a 2D cell culturing flask. Then, the iron oxide-Au—PL solution was added to the flask of cells (with concentrations ranging from 1.56-13.00 $\mu L/cm^2$) and allowed to incubate with the cells. The incubation time was approximately overnight (or ~12 hours). Primary cells were then washed with PBS (unbound iron oxide-Au—PL removed). Finally cells were detached by trypsin digestion, transferred to 3.5 cm Petri dishes and finally levitated with a ring shape neodymium magnet (20×(8.5×4.5)×7 mm; pull strength: 13 lbs).

All four types of nanoassemblies prepared with different forms and sizes of iron oxide adhered and were able to readily levitate cells (data not shown), even where the original cell contact employed adhered cells. However, the assemblies prepared with larger iron oxide (<5 μm, $Fe_3O_4$, magnetite) did not form as large and cohesive cell structures as did the others, indicating that there is an upper limit to the size of the magnetically responsive element that can be taken up by cells. Here, it is likely that smaller cell clusters result from the presence of the larger iron oxide particles that do not readily enter the cells, therefore the cells are less magnetized and such larger size particles may also coat the cell surface and hinder or impair cell-cell interaction.

Example

Ex Vivo Cell Levitation

Figure 7:
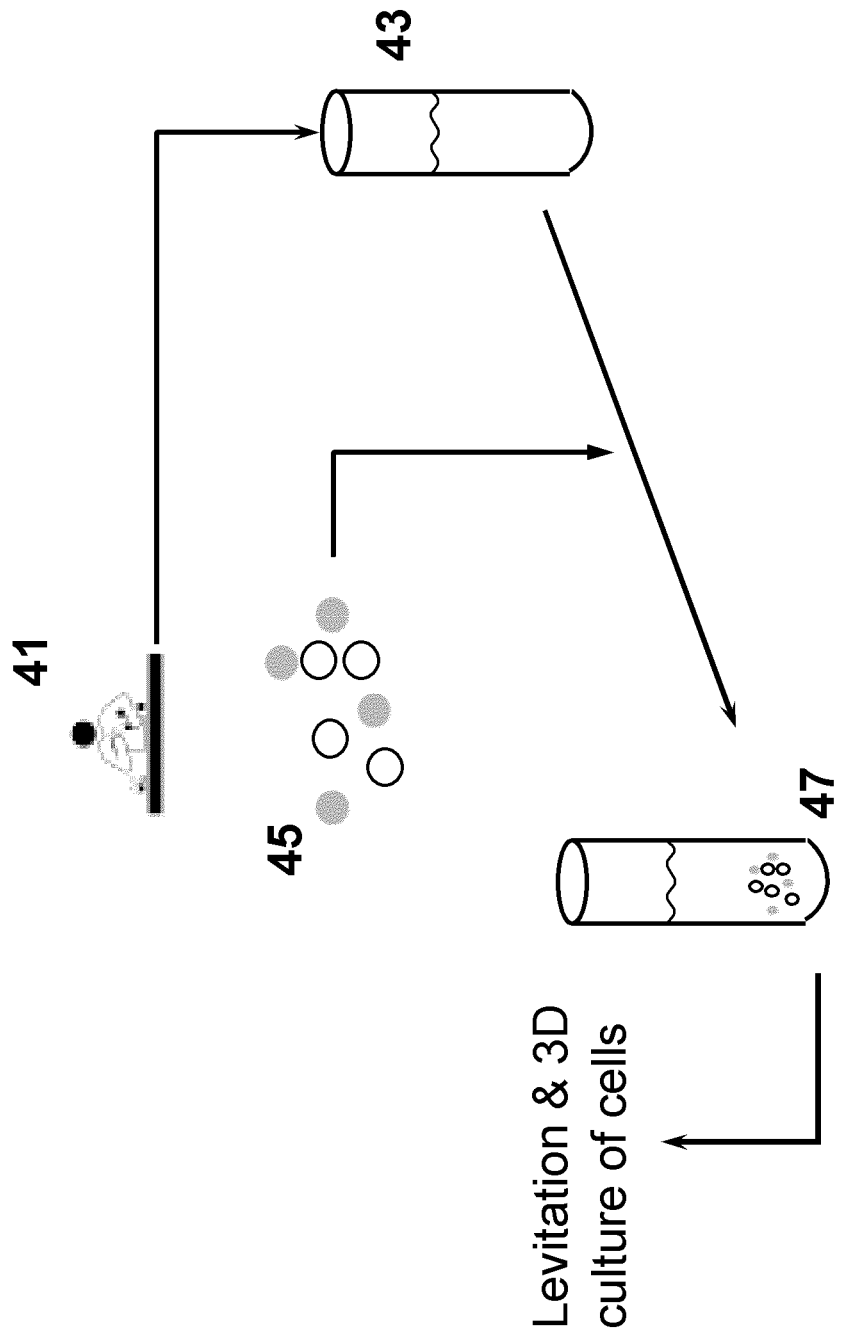
FIG. 7 is a schematic indicating the use of cells or fluid from an animal in the method of the invention.

Referring to FIG. 7, any cells taken from animals or humans (41), including, but not limited to, blood, serum, plasma, or disaggregated tissue cells (43), are mixed with nanoparticles (45) and then incubated together for 30 seconds to 48 hours. During incubation, the sample (43) and nanoparticles (43) interact electrostatically together with any proteins, DNA or polysaccharide that may be contained therein to form the nanoparticle assembly (47). Then, the magnetic nanoparticle assembly (47) is separated by magnetic force, centrifugation, and/or sedimentation, where the supernatant is separated from mixture, and a magnet used to manipulate the remaining magnetized cells.

Still referring to FIG. 7, the nanoparticle assembly is generated from the interaction between the proteins, DNA or polysaccharide present in the blood or other sample [43]. The types of interactions can include, but are not limited to, interactions of electrostatic nature, covalent (thiol functional groups and/or other cross-linkers), short range, and/or hydrophobic (usually through a bridging molecule) of specific and non-specific nature. For example, electrostatic interactions can be enabled and/or controlled by manipulation of pH, where proteins of different isoelectric points interact with their corresponding nanoparticle surface charges.

Furthermore, additional support molecules can also be added to the assembly to support cell growth or further bridge the various components of the assembly. This kind of bridging can be achieved by modifying the original sample (43) or the magnetic nanoparticle assembly (47) with antibodies or other molecules (for example peptides or protein tags), so specific molecules are enriched/captured in the assembly.

The embodiment described in herein can be of value for preparing nanoparticle assemblies with native proteins to reduce any immune response when the final cells are to be used therapeutically. This could be of significance when dealing with culturing cells for autologous cell procedures, since serum, blood, or other body tissues or fluids could be used to prepare the nanoparticle assemblies for masking foreign body effects.

Example

Frozen Magnetized Cells

We have shown herein, that cells can be frozen when magnetized, and then later thawed and used for 3D culturing. Cells are mixed with magnetic nanoparticle assembly per the procedures above. The excess magnetic nanoparticle assembly is then removed, and the cells washed and cryopreserved according to standard techniques. Later they are thawed, and cultured in a 3D culture system. This is very convenient, as it allows us to prepare and commercialize magnetized cells for use in research and therapeutics.

The following procedure was used. A flask of T-25 Human Embryonic Kidney (HEK293) cells (ATCC CRL-1573) were grown to 80% confluency and treated with 200 μL of iron oxide-Au—PL. After an ~12 hour incubation period. Then, cells were washed with PBS (unbound iron oxide-Au—PL removed), trypsinized, split into two vials, placed in DMSO-containing media, and then frozen at −80° C. The next day they were transferred into a liquid nitrogen dewar for long-term storage.

Eighty one days later, 1 vial was thawed in a water bath at 37° C. for 2 minutes. After resuspending the vial in 7.5 mL of media, the cells were split between three 35 mm diameter Petri dishes and 1000 G magnets were placed on top of each dish. The cells recovered from cryopreservation and they were cultured for days in 3D by magnetic levitation. We were able to grow satisfactory levitated 3D cultures using these cells. This procedure has also been successfully performed with primary smooth muscle cells, primary fibroblast cells, glioblastoma cells (LN299), and hepatoma (H4IIE cancer cells, hepatocarcinoma). Therefore, magnetized cells can be prepared in advance for later use.

Example

Cyclical Treatment

We can also perform multiple rounds of cell levitations, adding cell or cell extracts to existing 3D cultures. In this way, the cultures can be enriched for various cells or cellular products as the 3 d culture is grown.

Figure 8:
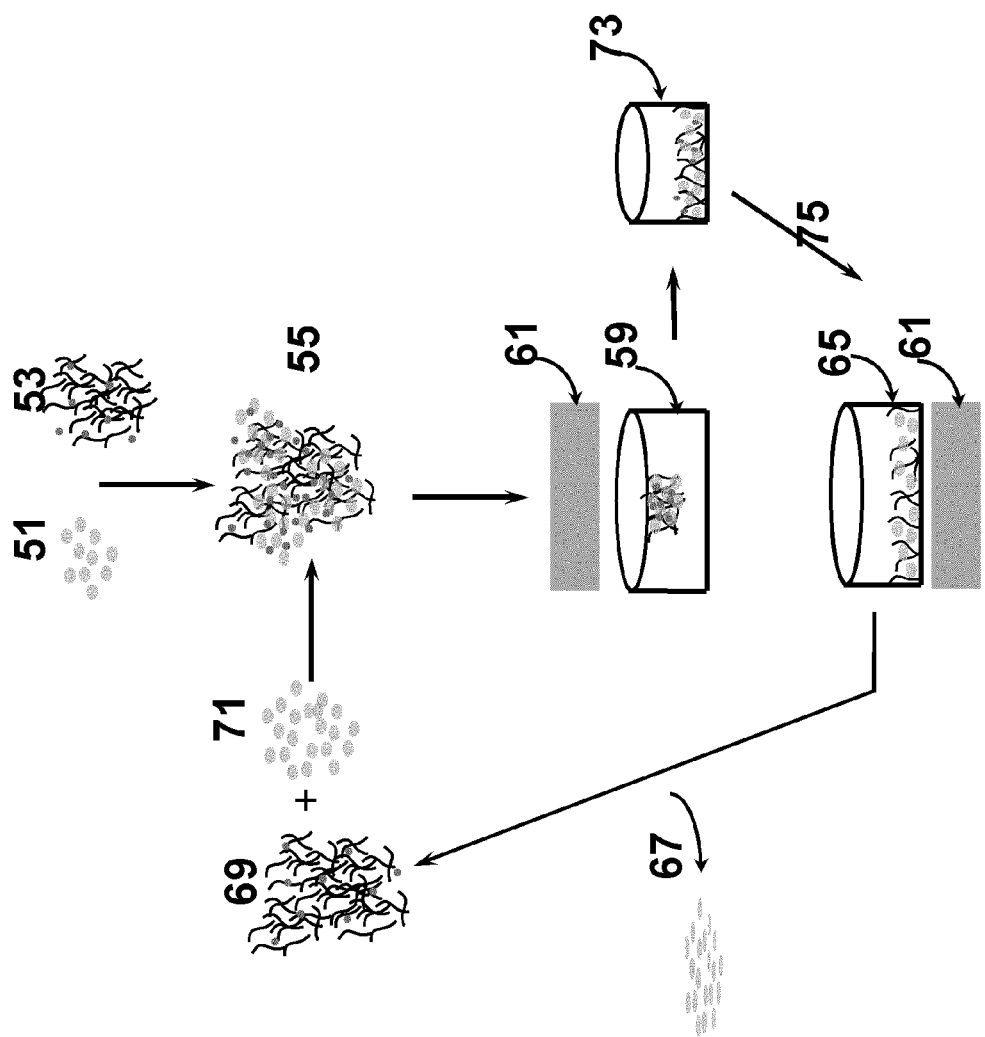
FIG. 8 is a schematic showing cyclical use of cell or extracts from the invention being added to already growing samples.
Figure 9:
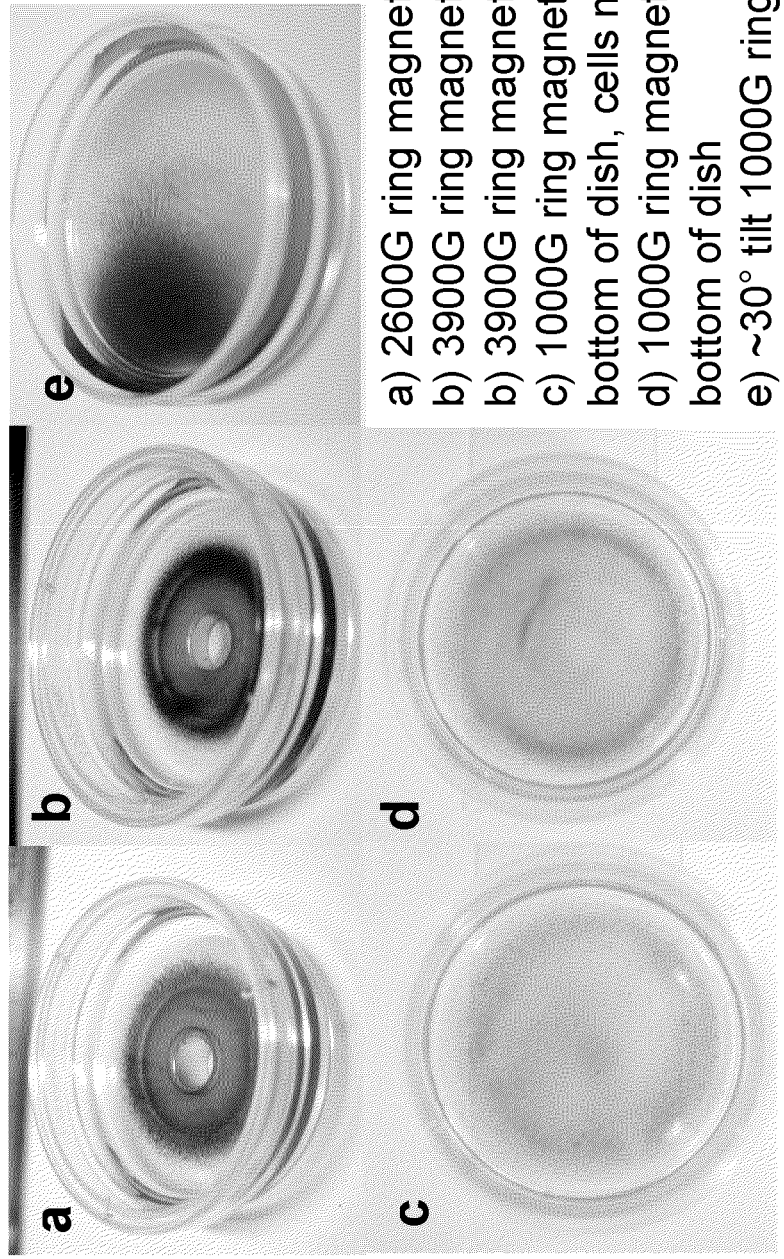
FIG. 9a-e shows photographs of several examples of manipulating cell density and shape using the methods of the invention.

In FIG. 8, cells (51) are added to a magnetic nanoparticle assembly (53) and the cells and magnetic nanoparticle assembly incubated together (55) to allow the cells to magnetize. Next, the magnetized cells are levitated (59) using a magnet (61). After, cells are levitated for 4 hours, overnight, or days (depending on cell type), cells were removed from levitation, media was replaced with picopure water (73), and cells were lysed by freeze-thaw action (75) (cells were placed in liquid nitrogen for at least 10 minutes). Alternatively, the cells can be pulled to the bottom of the culture dish (65) using a magnet (61), where this step can be repeated 1 to 4 times. Then either the cells (67) or a cell extract (69) or different cells (71) can be fed back into another sample and the 3D culturing process continued. Photographs are not shown, but these procedures have been successfully demonstrated.

Example

Shaped Cultures

We have also demonstrated that the shape of the 3D cell culture can be varied by modifying the magnetic field. The use of a strong magnet pulling the cells to the bottom of the plate, creates a fairly dense, well formed sheet of cells (not shown). This can then be levitated by reversing the magnetic field. We have also created 3D cultures that are thicker on one side by tilting the magnet. Donut shaped cultures were created with the use of toroidal magnets.

Figure 10:
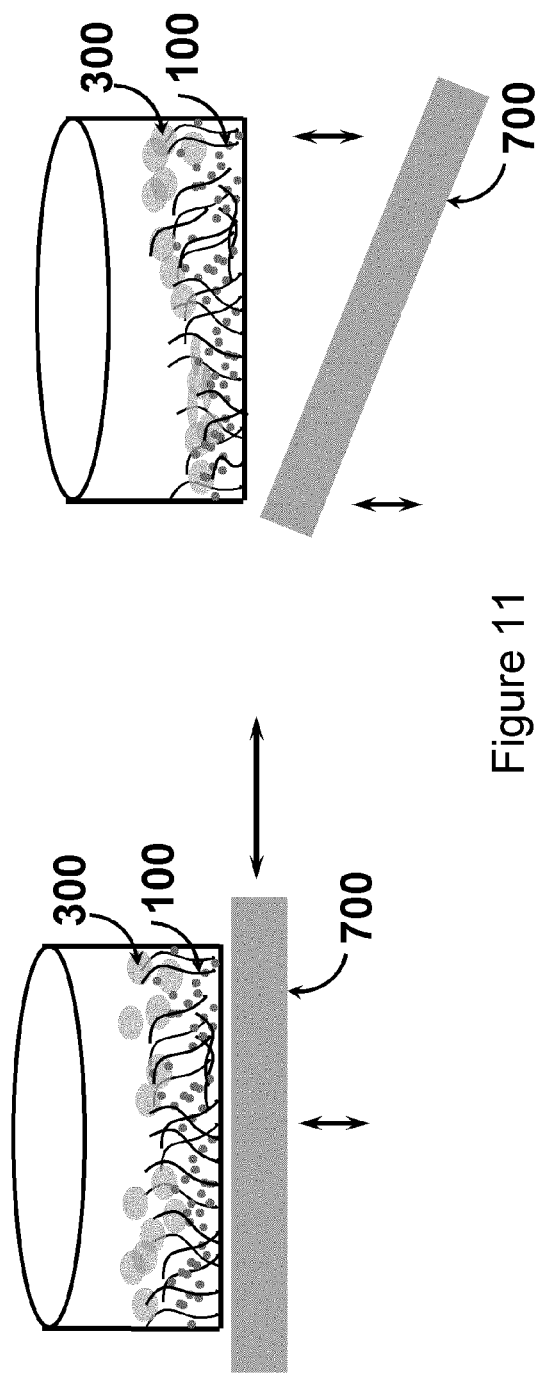
FIG. 10 showing changing 3D culture thickness by skewing the magnetic field.
Figure 11:
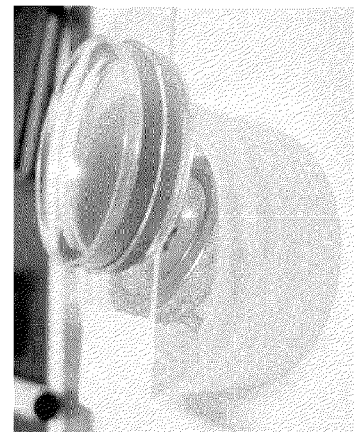
FIG. 11 is a photograph showing an example of the method of FIG. 10.

FIG. 9a-e for example, shows a few exemplary cell cultures where cells can be compressed more or less by varying the strength of the magnetic field, or distance of the magnet from the dish, and where toroid shaped are achieved using a ring magnet. FIGS. 10 and 11 show a 3D culture made thicker on one side by tilting the magnetic field.

We also predict that we can stack such donut shaped or sheet cell cultures, thus eventually creating more complex structures. For example, a tube like structure could be created by stacking discs. A compartment can be created by stacking disks, and then layering sheets on one or both ends, and the compartment could be filled with the same or different cell type. In this way, more complex tissue engineering can be accomplished.

We can also move cells using the magnetic field and that movement can affect the properties and composition of the 3D culture. When cells are seeded with the hydrogel (aka magnetic nanoparticle assembly), the vertical and/or horizontal motion of the magnetic fields, either by the motion of permanent magnets or by varying magnetic fields generated from electromagnets, prevents cells from attaching directly to the cell culture plate. The frequency of this motion can vary from, for example, 1 Hz (60 times per minute) to 0.001 Hz. Furthermore, different cell types could interact very differently with a moving gel. By combining vertical and/or horizontal motions, the stiffness of the moving material will further dictate the type of cells that would differentially adhere to the moving gel. A variation of this approach could also be achieved by applying a rocking motion to the magnet. This method is a valuable alternative for preparing, separating, and sorting cells for magnetic manipulation, including, but not limited to, 3D cell culturing by magnetic levitation.

Example

Surface Contact

In the above embodiments we mixed the magnetic nanoparticle assembly with the cells, thus providing an intimate admixture of the components. However, we have also shown that this is not necessary, and that merely being adjacent the magnetic nanoparticle assembly the cells will take up the magnetic nanoparticles. This is of benefit when the cells are needed to be free of magnetic nanoparticle assembly materials.

Figure 12:
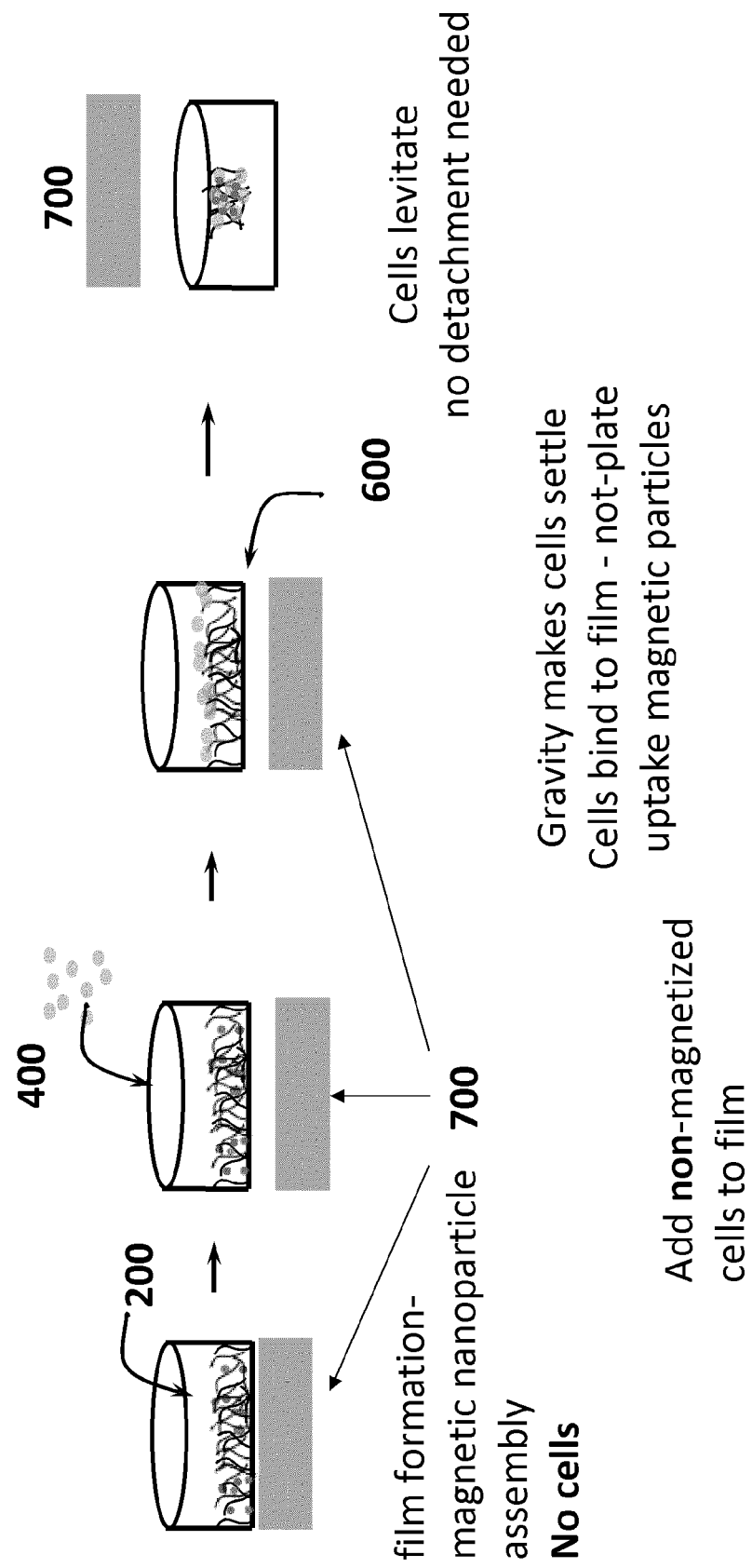
FIG. 12 is a schematic illustrating the use of a magnetic film to magnetized cells, where the cells are not intimately admixed with the magnetic nanoparticle assembly, but only sit on the surface thereof.

FIG. 12 illustrates the method whereby magnetic nanoparticle assembly (200) is exposed to a magnetic field. This has the effect of concentrating or compressing the magnetic nanoparticle assembly into a denser magnetic film. Cells (400) can be added above the film, and will naturally settle by gravity onto the film, and their proximity to the film will allow the cells to be magnetized. Then the cells can easily be levitated and separated from the film, levitated and grown in 3D culture. We have tested this concept with a wide variety of support molecules and demonstrated that it works.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

The following references are incorporated by reference in their entirety:

(1) Shimizu, K.; Ito, A.; Arinobe, M.; Murase, Y.; Iwata, Y.; Narita, Y.; Kagami, H.; Ueda, M.; Honda, H. *J. Biosci. Bioeng.* 2007, 103, 472-8.

(2) Kosmulski, M.; Marcel Dekker: *Chemical Properties of Material Surfaces*: New York, 2001.

(3) Mahmoudi, M.; Simchi, A.; Imani, M. *J. Iran. Chem. Soc.* 2010, 7, S1-S27.

(4) Bacri, J.-C.; Perzynski, R.; Salin, D.; Cabuil, V.; Massart, R. *J. Magn. Magn. Mater.* 1990, 85, 27-32.

(5) Douziech-Eyrolles, L.; Marchais, H.; Herve, K.; Munnier, E.; Souce, M.; Linassier, C.; Dubois, P.; Chourpa, I. *Int. J. Nanomed.* 2007, 2, 541-550.

(6) Duff, D. G.; Baiker, A.; Edwards, P. P. *Langmuir* 1993, 9, 2301-2309.

US2005054101, WO2005010162
US2009137018, WO2005003332
US2006063252, WO2004083412, WO2004083416
WO2010036957

The invention claimed is:

1. A method of growing a 3D cell culture, said method comprising:
   a) mixing cells with a composition comprising:
      i) a negatively charged nanoparticle;
      ii) a positively charged nanoparticle; and
      iii) a support molecule;
      iv) wherein one of said negatively charged nanoparticle or positively charged nanoparticle contains a magnetically responsive element, and wherein said support molecule holds said negatively charged nanoparticle and said positively charged nanoparticle in an intimate admixture forming a fibrous mat-like structure;
   b) incubating said mixture for 1 to 12 hours until the cells become magnetized;
   c) subjecting said magnetized cells to a magnetic field sufficient to levitate said magnetized cells; and d) growing said levitated cells to make a levitated 3D culture.

2. The method of claim 1, wherein said negatively charged nanoparticle is a gold nanoparticle.

3. The method of claim 1, wherein said positively charged nanoparticle is an iron oxide nanoparticle.

4. The method of claim 1, wherein the support molecule comprises peptides, polysaccharides, nucleic acids, polymers or combinations thereof.

5. The method of claim 1, wherein the support molecule comprises poly-lysine, fibronectin, collagen, laminin, BSA, hyaluronan, glycosaminoglycan, anionic, non-sulfated glycosaminoglycan, gelatin, nucleic acid, extracellular matrix proteins, cell extract, antibody or mixtures or derivatives thereof.

6. The method of claim 1, wherein the support molecule comprises poly-lysine.

7. The method of claim 1, wherein said composition comprises $FeO_2$—Au-poly-lysine.

8. The method of claim 1, wherein said magnetized cells are washed before being levitated.

9. The method of claim 1, wherein said cells are a mixture of more than one cell type.

10. The method of claim 1, wherein in step c) said magnetized cells are subject to a magnetic field which provides a specific shape sufficient to levitate and shape said magnetized cells; and in step d) the levitated cells are shaped by growing said levitated and shaped cells to make a levitated 3D culture having said shape.

11. The method of claim 10, wherein said magnetic field provides shapes which are: toroidal, spherical, circular, polygonal or line shaped and wherein said levitated 3D culture is toroidal, spherical, circular, polygonal or line shaped.

12. The method of claim 11, wherein a plurality of toroidal 3D cultures are stacked one on top of another to make a tubular 3D culture.

13. The method of claim 10, wherein said magnetic field provides shapes which are: toroidal, spherical, circular rectangular, or line shaped and wherein said levitated 3D culture is toroidal.

* * * * *